(12) United States Patent
Sandoval, Jr. et al.

(10) Patent No.: US 10,994,030 B2
(45) Date of Patent: *May 4, 2021

(54) COMPOSITIONS AND METHODS FOR MEASURING AND EXPANDING BLOOD VOLUME

(71) Applicant: PharmacoPhotonics, Inc., Carmel, IN (US)

(72) Inventors: Ruben Sandoval, Jr., Indianapolis, IN (US); Erinn Sheridan Reilly, Indianapolis, IN (US); Daniel Meier, Indianapolis, IN (US)

(73) Assignee: PHARMACOPHOTONICS, INC., Carmel, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/363,068

(22) Filed: Mar. 25, 2019

(65) Prior Publication Data

US 2020/0000941 A1    Jan. 2, 2020

Related U.S. Application Data

(63) Continuation of application No. 15/116,650, filed as application No. PCT/US2015/014845 on Feb. 6, 2015, now Pat. No. 10,279,052.

(60) Provisional application No. 61/936,981, filed on Feb. 7, 2014.

(51) Int. Cl.
| | |
|---|---|
| *A61K 49/00* | (2006.01) |
| *A61B 5/055* | (2006.01) |
| *A61K 38/38* | (2006.01) |
| *A61K 9/00* | (2006.01) |
| *A61K 31/00* | (2006.01) |
| *A61K 31/721* | (2006.01) |
| *G01N 33/49* | (2006.01) |

(52) U.S. Cl.
CPC ........ *A61K 49/0043* (2013.01); *A61K 9/0026* (2013.01); *A61K 31/00* (2013.01); *A61K 31/721* (2013.01); *A61K 38/38* (2013.01); *A61K 49/0041* (2013.01); *A61K 49/0054* (2013.01); *A61K 49/0056* (2013.01); *G01N 33/49* (2013.01)

(58) Field of Classification Search
CPC .. A61K 8/00117; A61K 8/0019; A61K 8/021; A61B 5/055
See application file for complete search history.

(56) References Cited

U.S. PATENT DOCUMENTS

| 6,355,624 B1 | 3/2002 | Jones et al. | |
|---|---|---|---|
| 10,279,052 B2* | 5/2019 | Sandoval, Jr. | ....... A61K 9/0026 |
| 2003/0004105 A1* | 1/2003 | Assaly | ................ A61K 38/018 514/13.5 |
| 2009/0285761 A1* | 11/2009 | Wang | .................... A61B 5/412 424/9.6 |
| 2012/0276014 A1* | 11/2012 | Molitoris | ........... A61K 49/0054 424/9.6 |

FOREIGN PATENT DOCUMENTS

EP    1093720 A1    4/2001

OTHER PUBLICATIONS

Extended European Search Report in corresponding European Application No. EP15746505.5 dated Oct. 2, 2017, pp. 1-3.
TdB Consultancy "FITC-Dextran" XP055408803 (2010) Retrieved from the Internet: URL: http://tdbcons.com/images/pdf/fitcdextran2.pdf.

* cited by examiner

*Primary Examiner* — Micah Paul Young
(74) *Attorney, Agent, or Firm* — Burns & Levinson LLP; Bruce D. Jobse

(57) ABSTRACT

A method for measuring, adjusting and maintaining the level of blood volume in a patient is described. A blood volume expander composition includes, in combination, a standard unmodified protein, colloid or crystalloid and a fluorescently-labeled protein, colloid or crystalloid of approximately the same molecular weight. The use of blood volume expanders to measure, adjust and maintain the level of blood volume in a patient also is described.

18 Claims, 4 Drawing Sheets

COMPOSITIONS AND METHODS FOR MEASURING AND EXPANDING BLOOD VOLUME

CROSS-REFERENCE TO RELATED APPLICATIONS

This application is a continuation of co-pending U.S. patent application Ser. No. 15/116,650, filed on Aug. 4, 2016, entitled COMPOSITIONS AND METHODS FOR MEASURING AND EXPANDING BLOOD VOLUME, which in turn is a U.S. national stage application under 35 U.S.C. 371 of International Application No. PCT/US2015/14845, filed on Feb. 6, 2015, which in turn claims priority to U.S. Provisional Patent Application No. 61/936,981, filed on Feb. 7, 2014, all of which are incorporated by reference herein in their entirety for all purposes.

BACKGROUND OF THE INVENTION

Volume expanders (or plasma volume expanders) are used in intravenous therapy for providing additional volume for the circulatory system, typically for fluid replacement, as the patient undergoes a medical procedure. Many volume expanders are typically based on solutions of dextrans of various molecular weights, but volume expanders can also include other biocompatible substances such as albumin.

Typical blood expanders used in clinical settings include normal saline, lactated Ringer's solution, albumin, and dextran. Dextran 40, as an example, is in widespread use as a volume expander. In addition to its volume-expanding effects, Dextran 40 is additionally able to improve microcirculation with a relatively low risk of antigenicity, and it can also be used with patients where there is a risk of thromboembolic complications. Dextran 40 has a molecular weight of 40 kDa, but other higher molecular weight dextrans, such as Dextran 70 and Dextran 75, are also used as volume expanders.

Blood volume measurement is important for the determination of proper drug dosing, pharmacokinetics, and blood pressure maintenance. Blood volume status and blood volume management are indicators of medical conditions such as end stage renal disease, acute kidney injury, chronic kidney disease, and acute blood loss. In addition, the evaluation of blood volume is important for dialysis patients since there are important implications with regard to the loss of blood volume while on dialysis. This is clinically important for the control of blood pressure and clinical outcomes in patients with end stage renal disease who require dialysis or renal replacement therapy for volume removal.

A commonly used technique for estimating blood volume is based on the indicator dilution technique in which an indicator molecule is mixed and distributed into an unknown volume. An identical amount of the indicator molecule is placed into a known volume. The unknown volume can be measured by comparing the concentration of the indicator between the known and unknown volume. A common indicator molecule is albumin labeled with various dyes, such as radioactive iodine, or the fluorescent dye indocyanine green (ICG). For example, Daxor Corporation (New York, N.Y.) has developed a device for measuring blood volume using albumin labeled with radioactive iodine as the tracer indicator. The use of ICG-labeled albumin as a tracer indicator has also been disclosed, with the ICG-labeled albumin measured by near infra-red absorption of the molecule. However, because albumin is also being cleared from the blood during the time that the test is being conducted, both the ICG and radiolabeled methods require a rapid succession of precisely timed blood draws in order to back calculate and estimate the peak concentration of the exogenously introduced albumin at the time when it was fully distributed throughout the vascular compartment. The process of taking a succession of five or more blood draws is logistically challenging in busy hospital and critical care environments. Additionally, radiolabeled albumin has a very limited shelf life, and use of radioactive materials requires special handling procedures, and limits the environments where both testing and analysis can occur.

Current technology does not permit a determination of the plasma volume expander concentration in the patient's plasma because the volume expanders do not include a detectable marker, such as a fluorescent label, which is capable of providing the timeliest data on concentration. This can have a significant impact on biometric parameters, such as glomerular filtration rate (GFR) an important kidney function parameter. For instance, blood loss can potentially lead to a reduction in GFR values, while the addition of excess plasma volume expander may exacerbate the reduction in GFR. Using current technology, a clinician can continue to administer a plasma volume expander to a kidney patient in an effort to maintain the plasma volume to the point where the GFR stops due to an elevated level of plasma volume expander beyond efficacious levels.

It will be readily appreciated that there is a clinical need to develop a minimally invasive method to accurately and inexpensively measure blood volume and critical organ function. The present invention is provided to solve the problems discussed above and other problems, and to provide advantages and aspects not provided by prior techniques. A full discussion of the features and advantages of the present invention is deferred to the following detailed description.

SUMMARY OF THE INVENTION

According to the disclosure, blood volume expander compositions are provided. The blood volume expander compositions include an unmodified protein, unmodified colloid or unmodified crystalloid, and a fluorescently-labeled protein, fluorescently-labeled colloid or fluorescently-labeled crystalloid having a first excitation wavelength and a first emission wavelength, the fluorescently-labeled protein, fluorescently-labeled colloid or fluorescently-labeled crystalloid being dynamic within the patient.

In various illustrative embodiments, the unmodified protein and the fluorescently-labeled protein are albumin; the unmodified crystalloid and the fluorescently-labeled crystalloid are normal saline or lactated Ringer's solution; and the unmodified colloid and the fluorescently-labeled colloid are gelatin, hetastarch or dextran. In an alternative embodiment, the unmodified crystalloid is normal saline or lactated Ringer's solution and the fluorescently-labeled tracer marker is a fluorescently labeled protein or colloid.

In further illustrative embodiments, the fluorescently-labeled protein, colloid or crystalloid is a dynamic molecule with a molecular weight of less than about 75 kDa, preferably about 40 Kda. Such dynamic molecules with a molecular weight of less than about 75 kDa include, for example normal saline, lactated Ringer's solution, gelatin, hetastarch, albumin and dextran.

In one illustrative embodiment, the unmodified colloid is Dextran 40, Dextran 70 or Dextran 75.

In another illustrative embodiment, the unmodified protein is albumin.

In another illustrative embodiment, the unmodified colloid is gelatin or hetastarch.

In yet another illustrative embodiment, the unmodified crystalloid is normal saline or lactated Ringer's solution.

In further illustrative embodiments, the amount of fluorescently-labeled protein, colloid or crystalloid is present in an amount of from about 0.01% to about 10.0% by weight of unmodified protein, colloid or crystalloid, preferably 0.01% to about 1.0% by weight of unmodified protein, colloid or crystalloid, more preferably about 0.1% by weight of unmodified protein, colloid or crystalloid.

In further illustrative embodiments, the fluorescently-labeled protein or colloid is prepared by conjugating a protein or colloid with at least one fluorescent compound. Fluorescent compounds include, but are not limited to, Texas Red, fluorescein isothiocyanate (FITC) and 2-SulfhydroRhodamine (2SHR). In certain preferred embodiments, the fluorescent compound is fluorescein isothiocyanate (FITC).

Also according to the disclosure is described methods for measuring and maintaining blood volume in a patient by administering a fluorescently-labeled static molecule to the vascular system of a patient, the static molecule having a second excitation wavelength and a second emission wavelength, and the static molecule being non-metabolized within the patient; obtaining a first blood sample from the patient or making a first non-invasive measurement of the blood of the patient after the static molecule has reached a fully distributed steady state concentration in the vascular system, and calculating the initial plasma volume based on the emission level in the sample; administering a blood volume expander to the vascular system of the patient; obtaining additional blood samples or non-invasive measurements from the patient following administration of the blood volume expander, and measuring the loss of blood volume expander from the patient.

In certain illustrative embodiments, the method further includes adding supplemental blood volume expander to the patient as needed.

In further illustrative embodiments of the method, a series of additional blood samples are taken from the patient or a series of additional non-invasive measurements are made at time intervals of between about 10 and 20 minutes.

In other illustrative embodiments of the method, the additional blood samples are continuously taken through an indwelling venous catheter or the additional non-invasive measurements are continuously made using an optical sensor.

In yet other illustrative embodiments of the method, the patient is suffering from kidney disease, acute renal failure or chronic renal failure.

In other illustrative embodiments of the method, the patient is suffering from blood loss due to trauma.

In further illustrative embodiments of the method, the fluorescently-labeled static molecule is a dextran with a molecular weight greater than about 75 kDa, preferably a dextran with a molecular weight of 150 kDa; and preferably labeled with 2-SulfhydroRhodamine (2SHR).

Also according to the disclosure is described the use of a blood volume expander composition for the manufacture of a medicament for measuring, adjusting and maintaining blood volume in a patient.

In an illustrative embodiment of the use of blood volume expander compositions, the composition is an unmodified protein, unmodified colloid or unmodified crystalloid, and a fluorescently-labeled protein, fluorescently-labeled colloid or fluorescently-labeled crystalloid having a first excitation wavelength and a first emission wavelength, said fluorescently-labeled protein, fluorescently-labeled colloid or fluorescently-labeled crystalloid being non-metabolized within the patient.

In various illustrative embodiments of the use of blood volume expander compositions, the unmodified protein and the fluorescently-labeled protein are albumin; the unmodified crystalloid and the fluorescently-labeled crystalloid are normal saline or lactated Ringer's solution; and the unmodified colloid and the fluorescently-labeled colloid are gelatin, hetastarch or dextran. In an alternative embodiment of the use of blood volume expander compositions, the unmodified crystalloid is normal saline or lactated Ringer's solution and the fluorescently-labeled tracer marker is a fluorescently labeled protein or colloid.

In further illustrative embodiments of the use of blood volume expander compositions, the fluorescently-labeled protein, colloid or crystalloid is a dynamic molecule with a molecular weight of less than about 75 kDa, preferably about 40 Kda. Such dynamic molecules with a molecular weight of less than about 75 kDa include, for example normal saline, lactated Ringer's solution, gelatin, hetastarch, albumin and dextran.

In one illustrative embodiment of the use of blood volume expander compositions, the unmodified colloid is Dextran 40, Dextran 70 or Dextran 75.

In another illustrative embodiment of the use of blood volume expander compositions, the unmodified protein is albumin.

In another illustrative embodiment of the use of blood volume expander compositions, the unmodified colloid is gelatin or hetastarch.

In yet another illustrative embodiment of the use of blood volume expander compositions, the unmodified crystalloid is normal saline or lactated Ringer's solution.

In further illustrative embodiments, the amount of fluorescently-labeled protein, colloid or crystalloid is present in an amount of from about 0.01% to about 10.0% by weight of unmodified protein, colloid or crystalloid, preferably 0.01% to about 1.0% by weight of unmodified protein, colloid or crystalloid, more preferably about 0.1% by weight of unmodified protein, colloid or crystalloid.

In further illustrative embodiments of the use of blood volume expander compositions, the fluorescently-labeled protein or colloid is prepared by conjugating a protein or colloid with at least one fluorescent compound. Fluorescent compounds include, but are not limited to, Texas Red, fluorescein isothiocyanate (FITC) and 2-SulfhydroRhodamine (2SHR). In certain preferred embodiments, the fluorescent compound is fluorescein isothiocyanate (FITC).

In yet other illustrative embodiments of the use of blood volume expander compositions, the patient is suffering from kidney disease, acute renal failure or chronic renal failure.

In other illustrative embodiments of the use of blood volume expander compositions, the patient is suffering from blood loss due to trauma.

According to the disclosure, the problems identified in the background as discussed above can be reduced or eliminated through the use of the plasma volume expanders, which incorporate a tracer compatible with the plasma volume expander, such as albumin "spiked" with a small amount of fluorescent albumin or dextran "spiked" with a small amount of a fluorescently-labeled dextran of similar, approximately identical, or identical molecular weight and dispersion characteristics. Accordingly, blood samples can be periodically or continuously taken from the patient, and the plasma volume concentration can be determined, thereby preventing an over-administration of the expander to the point where renal function can be impaired.

Compositions also are disclosed that include unmodified dextrans as the plasma expander base combined with dextrans which have been labeled with a fluorescent marker added to the base. The labeled dextrans are compatible with the unmodified dextrans and can be used to measure their concentration within the plasma in a patient undergoing volume replacement therapy.

In an illustrative embodiment, methods for the measurement, adjustment and maintenance of blood volume levels in a patient are accomplished by the use of a fluorescently-labeled detector molecule which is administered to the vascular system of a patient, followed by the administration of a blood volume expander having a different fluorescent characteristic. The first injected fluorescently-labeled molecule is used to make an initial determination of blood volume by taking a blood sample from the patient when equilibrium conditions have been established, and calculating the initial blood volume based on the fluorescent emission level of the sample. Following the initial measurement of blood volume, a blood volume expander containing tracer amounts of a differently fluorescent molecule is administered to the patient. Blood volumes can then be adjusted and maintained at the desired level for each individual patient. Blood loss or leakage from the patient can be monitored based on the rate of blood replenishments, or through the use of the novel blood volume expander compositions as described herein.

In another illustrative embodiment, the fluorescently-labeled molecule is a large molecular weight dextran (>about 75 kDa) conjugated to one or more fluorescent markers. Preferably, the fluorescently-labeled dextran has a molecular weight of 150 kDA or more and is resident or "static" in the vascular system of the patient, meaning that it remains in the vascular system and is relatively impermeable, i.e. it does not penetrate the blood vessel walls, and is not metabolized, i.e. it is not immediately removed from the vascular space through a metabolic function of the body or an immunological response. The fluorescently-labeled dextran can be prepared by conjugating a fluorescent molecule and a macromolecule such as dextran in a conjugation reaction. Preferably, the fluorescent molecule is a compound selected from the group consisting of Texas Red, fluorescein isothiocyanate (FITC) and 2-SulfhydroRhodamine (2SHR), with 2SHR being especially preferred. Suitable techniques for preparing such molecules and deploying the molecules for measuring blood volume levels are disclosed in copending PCT patent application no. PCT/US2013/026277, the disclosure of which is incorporated by reference herein.

In another illustrative embodiment, novel blood volume expander compositions are provided. Such compositions are prepared by supplementing an unmodified or standard dextran-based volume expander with a small amount of a fluorescently-labeled dextran (of a different fluorescent property than the "static" marker). The unmodified dextran volume expander is supplemented with from about 0.01% to about 10.0% by weight of fluorescently-labeled dextran, preferably about 0.01% to about 1.0% by weight, more preferably about 0.1% by weight. The fluorescently-labeled dextran is fully compatible with, and similar, nearly identical or identical in molecular weight and size dispersion to the unmodified dextran volume expander; preferably taken from the identical production lot number. After an initial plasma volume determination for the patient has been made, periodic or continual blood samples are taken to determine the change in plasma volume based on the level of fluorescent emissions in the sample using known analytical relationships as described herein.

In yet another illustrative embodiment, the unmodified or standardized volume expander is a molecule having a molecular weight of 75 kDa or less. For example the unmodified or standardized volume expander can be albumin (66.5 kDa) or Dextran 40, 70 or 75, i.e. a dextran having a molecular weight of 40 kDa, 70 kDa or 75 kDa, respectively. The lower the molecular weight the more readily permeable in the vascular system, i.e. it is capable of penetrating the vessel walls of the patient.

In a further illustrative embodiment, a method for measuring blood volume in a patient comprises the following steps. An initial determination of the blood volume of the patient is made by administering a fluorescently-labeled static molecule to the patient, a blood sample is taken when equilibrium conditions have been established, and the initial blood volume is calculated based on the fluorescent emission level of the sample. Following the initial measurement of blood volume, a blood volume expander is administered to the patient, and a second and possibly, further sets of blood samples are periodically taken once the volume expander has fully distributed and caused an increase in plasma volume. Alternatively, the blood volume can be continuously monitored using a blood line from the patient or through non-invasive techniques, such as with an external optical sensor.

In one aspect of this embodiment, the patient is suffering from a medical condition such as kidney disease, acute or chronic renal failure, or acute blood loss.

Other features and advantages of the present novel technology will be apparent from the following description.

BRIEF DESCRIPTION OF THE DRAWINGS

To understand the present invention, it will now be described by way of example with reference to the accompanying drawings in which.

DETAILED DESCRIPTION

Figure 1:
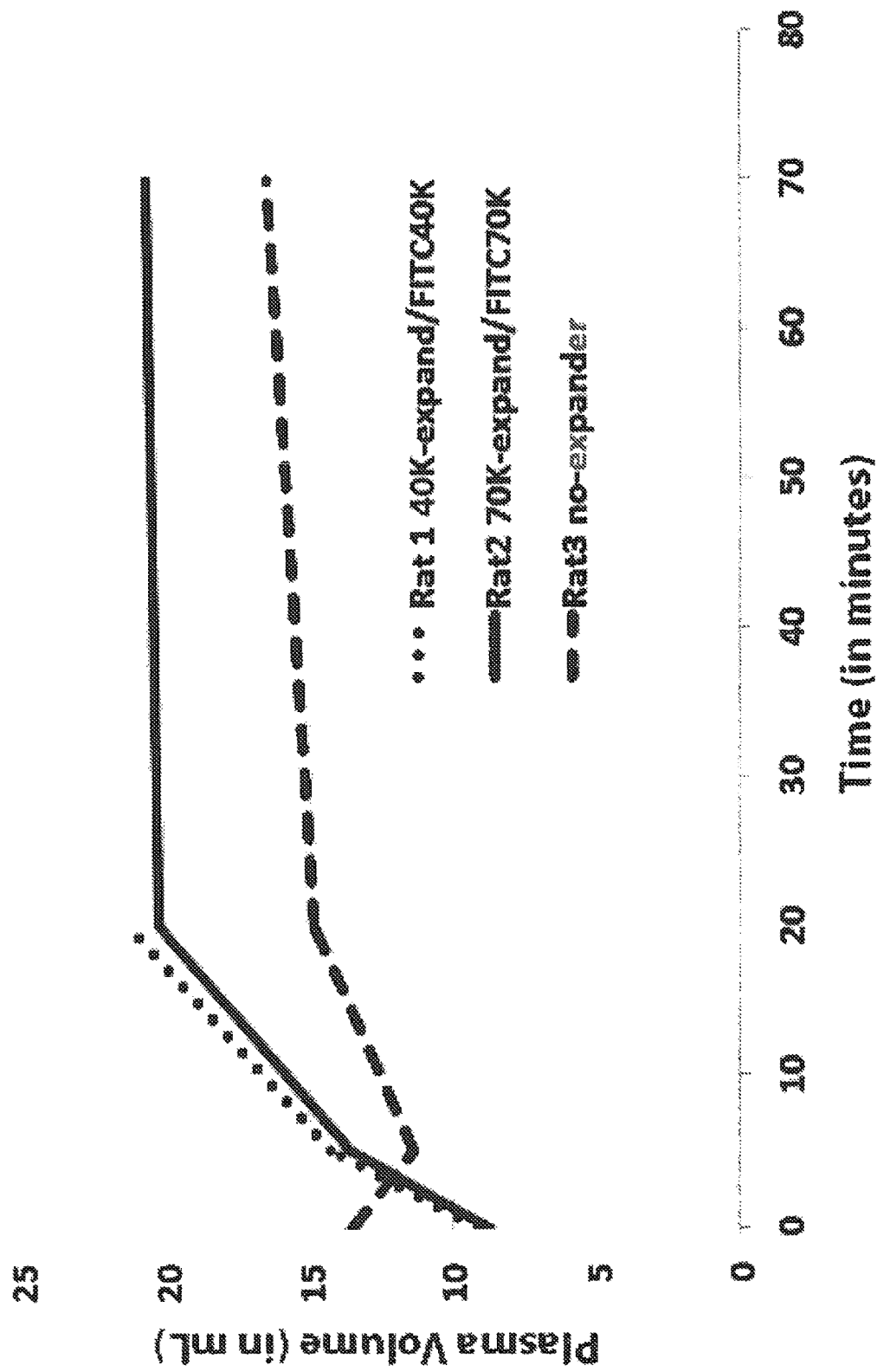
FIG. 1 is a graph showing plasma volume (as determined using a "static" 150 kDa 2SHR dextran) over time for two exemplary volume expander mixtures in two different partially exsanguinated rats: a 40 kDa dextran spiked with a fluorescein-isothiocyanate ("FITC") dextran tracer of 40 kDa dextran, and a 70 kDa dextran spiked with a tracer FITC 70 kDa dextran. A third rat subjected to partial exsanguination and given identical saline volume but not treated with an expander was used as a control.

For the purposes of promoting an understanding of the principles of the invention, reference will be made to the embodiments illustrated in the drawings, and specific language will be used to describe the same. It will nevertheless be understood that these embodiments constitute no limitation as to the scope of the invention, with alterations and further modifications being permissible, and such further applications of the principles of the technology as illustrated therein, being contemplated as would normally occur to one skilled in the art to which the technology relates.

Described herein are methods for determining, adjusting and maintaining plasma levels in a patient receiving a blood volume expander as part of a therapeutic program or treatment regime. Also described herein are improved blood volume expanders for directly measuring the amount of expander in a patient undergoing treatment. Also described herein are uses of the improved blood volume expanders for the manufacture of a medicament for measuring, adjusting and maintaining blood volume in a patient.

A fluorescently-labeled dextran is incorporated in a dextran-based plasma volume expander (i.e. a small known amount of fluorescently-labeled dextran is mixed into a known amount of non-fluorescent dextran) to permit the direct measurement of the amount of expander by measuring the intensity of the signal generated by the fluorescent marker in the volume expander.

Accordingly, and as may be used herein, the term "biological marker" or "biomarker" is intended to denote a molecular entity designed to be introduced into the vascular system of an animal, preferably a human subject, primarily to measure the function of an organ or vasculature of the animal. It is a biocompatible molecule formed as the conjugation product of one or more fluorescent molecules or dyes and a macromolecule.

The terms "volume expander", "blood volume expander", and "plasma volume expander" are used synonymously herein and designate biocompatible compositions designed to restore vascular volume, stabilize circulatory haemodynamics, and maintain tissue perfusion. Typical blood volume expanders include saline, albumin and dextran, such as Dextran 40, Dextran 70 and Dextran 75, where the numerical designations refer to the molecular weight of the dextran.

An "unmodified" or "standard" blood volume expander is a blood volume expander typically given to a patient in a clinical setting, and which does not include a labeled fluorescent component or molecule, or any other type of label or marker as a detection mechanism.

The "blood volume" or "plasma volume" as used herein denotes the amount of plasma volume within the vascular space including arterial, venous and capillary spaces. The blood volume does not include the volume contributed by the blood cells, such as the red blood cells. The total blood volume is the blood volume and the volume contributed by the blood cells, which can be determined from the hematocrit or the packed cell volume.

A "non-metabolized" molecule, or a molecule which is "not metabolized within the subject", as used herein, is a molecule which is not significantly metabolized during the time in which the measurements are performed. Such molecules typically have a half life of 4 hours or greater in the vascular system of the subject.

By "permeable to vessel walls" is meant a molecule that can cross vessel walls. Similarly, "impermeable to vessel walls" means that the molecule cannot cross the vessel walls either through a passive process or an active process.

A "dynamic molecule" is a molecule of sufficiently low molecular mass to permeate the blood vessel walls or the vasculature of a subject. These molecules are also cleared by the kidney via glomerular filtration with a decrease in clearance as molecular weight increases. Dynamic molecules are known in the art to have a molecular mass of less than about 75 kDa.

A "static molecule" is a molecule of sufficiently high molecular mass to significantly limit its blood vessel wall permeability and metabolism. Static molecules or markers may reach a quasi-stable vascular concentration for a period of time, although such markers may ultimately be cleared from the vasculature. Static markers are known in the art to have a molecular mass greater than about 75 kDa, preferably about 150 kDa. Such markers can remain in the vasculature for a time period of between about 1 or 2 hours, up to 12 hours or longer, depending on the molecular mass of the marker and rate of metabolism of the marker.

The term "fluorescently-labeled crystalloid" as used herein refers to adding a free, unconjugated fluorescent dye such as FITC into the solution.

According to the disclosure, the blood volume of a patient can be conveniently measured, adjusted and maintained using the techniques and compositions described herein. An initial assessment of the patient's blood volume is conducted, and once the initial assessment is completed, any loss in blood can be supplemented by administering a blood volume expander to the patient. Blood volume can be measured directly by utilizing a static fluorescent molecule introduced into the vascular system of the subject by techniques such as disclosed, for instance, in published PCT application PCT/US2013/026277, filed Feb. 15, 2013, the disclosure of which is incorporated herein in its entirety by reference. This procedure, in general, involves the administration of a static marker suitable for the measurement of initial plasma levels in a subject. The static marker can be a fluorescently-labeled dextran having a molecular weight greater than about 75 kDa to about 500 kDA, and preferably about 150 kDa. The fluorescent moiety used to label the dextran can be any of a variety of fluorescent molecules having a fluorescent excitation wavelength and an emission wavelength.

The fluorescent moiety is conjugated with the dextran in a conjugation reaction by covalent attachment. The fluorescent molecule can be a fluorescent dye marker such as a rhodamine dye. Suitable fluorescent molecules include, by way of example, Texas Red, fluorescein isothiocyanate (FITC) and 2-sulfurhodamine (2SHR), with 2SHR being preferred.

The static marker is introduced into the subject by, for instance, intravenous injection, and a blood sample can be taken after about 20 to 30 minutes once the volume expander has fully distributed. The sample can be taken using an indwelling venous catheter or a measurement can be made after about 20 to 30 minutes using a non-invasive sensor, such as a non-invasive optical sensor. The blood sample can be analyzed to establish the blood plasma level as described in PCT application no. PCT/US2013/026277.

The use of fluorescently-labeled molecules to evaluate the physical condition of a subject by introducing the molecule into the vascular system of a subject has been disclosed. Suitable methods and materials can be found in U.S. patent application Ser. No. 12/425,827, filed Apr. 17, 2009 and U.S. patent application Ser. No. 12/946,471, filed Nov. 15, 2010, the respective disclosures of which are incorporated herein in their entirety by reference thereto.

In general, according to the foregoing methods, a fluorescently-labeled macromolecule is introduced into the vascular system of a subject, such as by intravenous injection. Once equilibrium has been reached, blood samples can be periodically withdrawn, every 10 to 20 minutes for example, and the samples are analyzed for fluorescence in a medium formed from the sample, a buffering solution and an anionic surfactant. The analysis is conducted using a light source to activate the fluorescent molecule, and a light detector is used to measure and quantify the intensity of the fluorescent signal generated by the activated molecule. The biometric parameter under evaluation (blood volume) can be efficiently determined by comparing the values obtained from the samples of the subject with samples from a known source.

The blood volume expander can be any of a variety of blood volume expanders typically used by a clinician. Suitable blood volume expanders include, for example, saline, albumin and dextran. In a typical clinical environment, the blood volume expander is administered to a subject in order to adjust and maintain the subject's blood volume at a predetermined level. Loss of blood typically occurs as a result of the treatment of the patient for a medical condition wherein blood loss is a significant factor or result. These conditions include severe trauma due to external injuries, and chronic renal disease and/or failure.

The preferred blood volume expander is an unmodified or standard dextran solution, such as Dextran 40, Dextran 70 or Dextran 75. The blood volume expander is "doped" or supplemented with a relatively small amount of a fluorescently-labeled dextran, typically from about 0.01% to about 10.0% by weight, preferably from about 0.01% to about 1.0% by weight, more preferably about 0.1% by weight. The blood volume expander itself is typically an aqueous solution of dextran on the order of 5% or 6% of dextran by weight.

The fluorescently labeled dextran can advantageously have about the same, near identical or identical molecular weight as the unmodified dextran. As noted, a dynamic molecule has a sufficiently low molecular weight to penetrate the blood vessel walls or vasculature of the patient. Therefore, the amount of the molecule in the vasculature will change over time, and this change can be recorded, measured, and correlated with a biological parameter of interest, such as the level of blood volume.

The fluorescently-labeled dextran can be prepared by conjugating a fluorescent molecule with dextran using reaction techniques and conditions well known in the art. Typical fluorescent molecules which are suitable for conjugation include Texas Red, fluorescein isothiocyanate (FITC), and 2-SulfhydroRhodamine (2SHR), with fluorescein being preferred. The "doped" marker dextran in the expander must have a different fluorescent marker than the "static" 150 kDa dextran, which is preferably labeled with 2SHR.

According to the disclosure, a blood sample can be taken from a patient on a continuous or periodic basis, and the level of the volume expander in the blood can be measured by recording and correlating the presence of the dynamic molecule in the blood sample with the blood volume. This technique can be used to provide an accurate real time measurement of blood volume.

The methods and compositions described herein can be typically used in a clinic or hospital where the treatment of renal disease and renal failure are indicated.

The invention is further illustrated by the examples provided below, which are directed to certain embodiments of the invention and are not intended to limit the full scope of the invention as set forth in the appended claims.

Examples

A 13.6 mg dose of a 2SHR labeled dextran (150 kDa) is administered to a subject, and a blood sample is withdrawn after about 20 to 30 minutes to determine blood plasma volume using the procedure described in PCT application no. PCT/US2013/026277. This blood plasma level is recorded and used as a reference level for additional blood plasma volume measurements.

Figure 2:
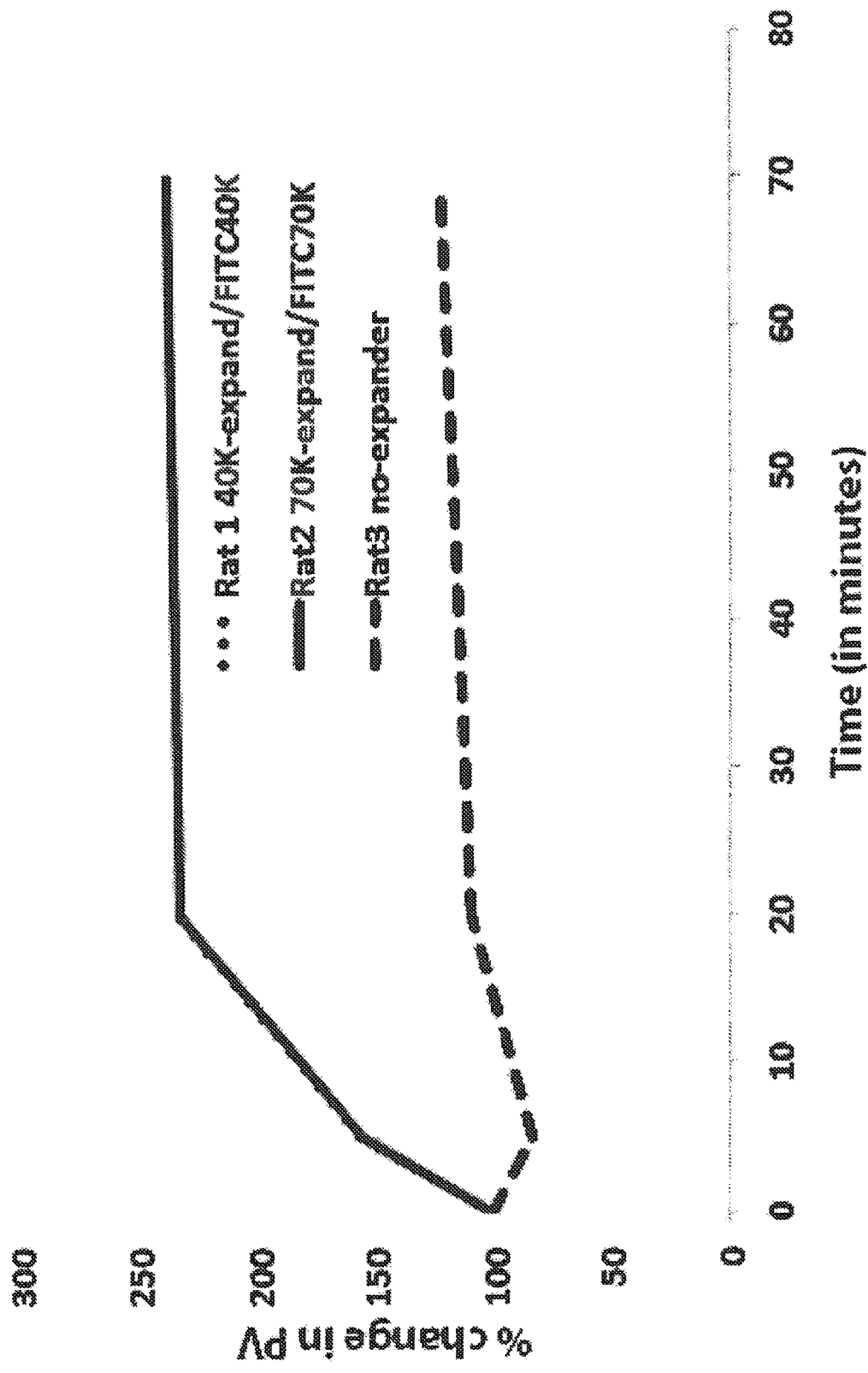
FIG. 2 is a graph showing plasma volume (as determined by using a "static" 150 kDa 2SHR dextran) as a percent increase of initial volume over time for two exemplary volume expander mixtures in two different partially exsanguinated rats: a 40 kDa dextran spiked with a tracer FITC 40 kDa dextran, and a 70 kDa dextran spiked with a tracer FITC 70 kDa dextran. A third rat subject to partial exsanguinations and given identical saline volume but not treated with an expander was used as a control. The values are expressed as a % of the control changes in order to highlight the large plasma volume change that occurs with the expanders but not with the exsanguinated rat given identical saline volume but not an expander. The increase for rats 1 and 2 are identical with overlapping graph indicators.
Figure 3:
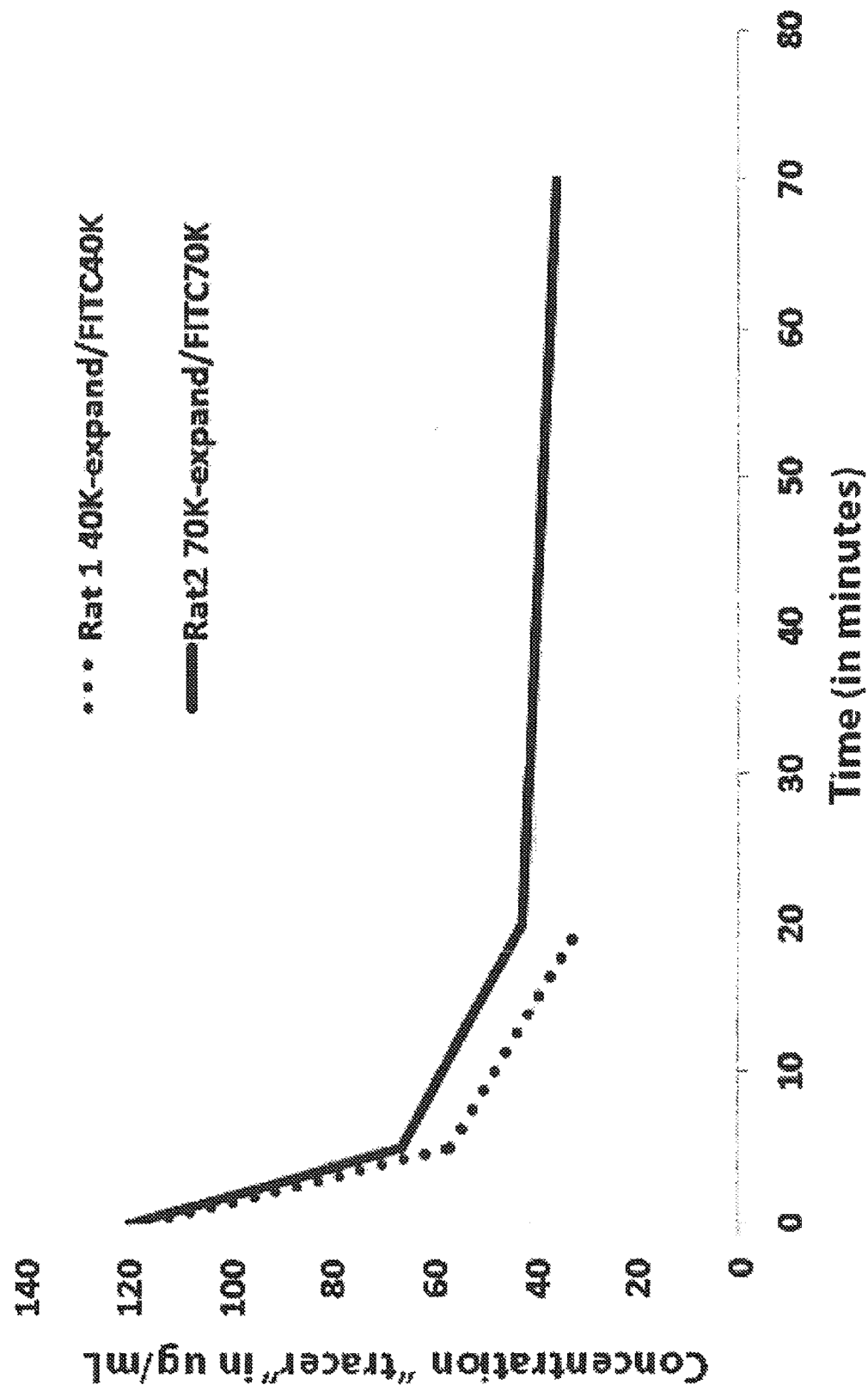
FIG. 3 is a graph showing the decay in concentration over time for two exemplary volume expanders: a 40 kDa dextran spiked with a tracer FITC 40 kDa dextran, and a 70 kDa dextran spiked with a tracer FITC 70 kDa dextran. This graph illustrates that with this method it is possible to determine the concentration of the plasma expander by standard spectrophotometric methods and dilution principles.

Next, a standard dose of a Dextran 40 or Dextran 70 blood volume expander is administered to the subject with a small amount of a fluorescently-tagged dextran of approximately the same molecular weight added to the blood volume expander. For purposes of the example, a 30 gram solution of Dextran 40 or Dextran 70 is formulated with about 30 mg of approximately the same molecular weight dextran conjugated to Fluorescein (FITC) (or about 0.1% of fluorescently-labeled dextran by weight of unmodified dextran). Blood plasma volume and fluorescent concentration (ug/mL) are recorded as a function of time for Dextran 40 and Dextran 70. The results are shown in FIGS. 1, 2 and 3.

Figure 4:
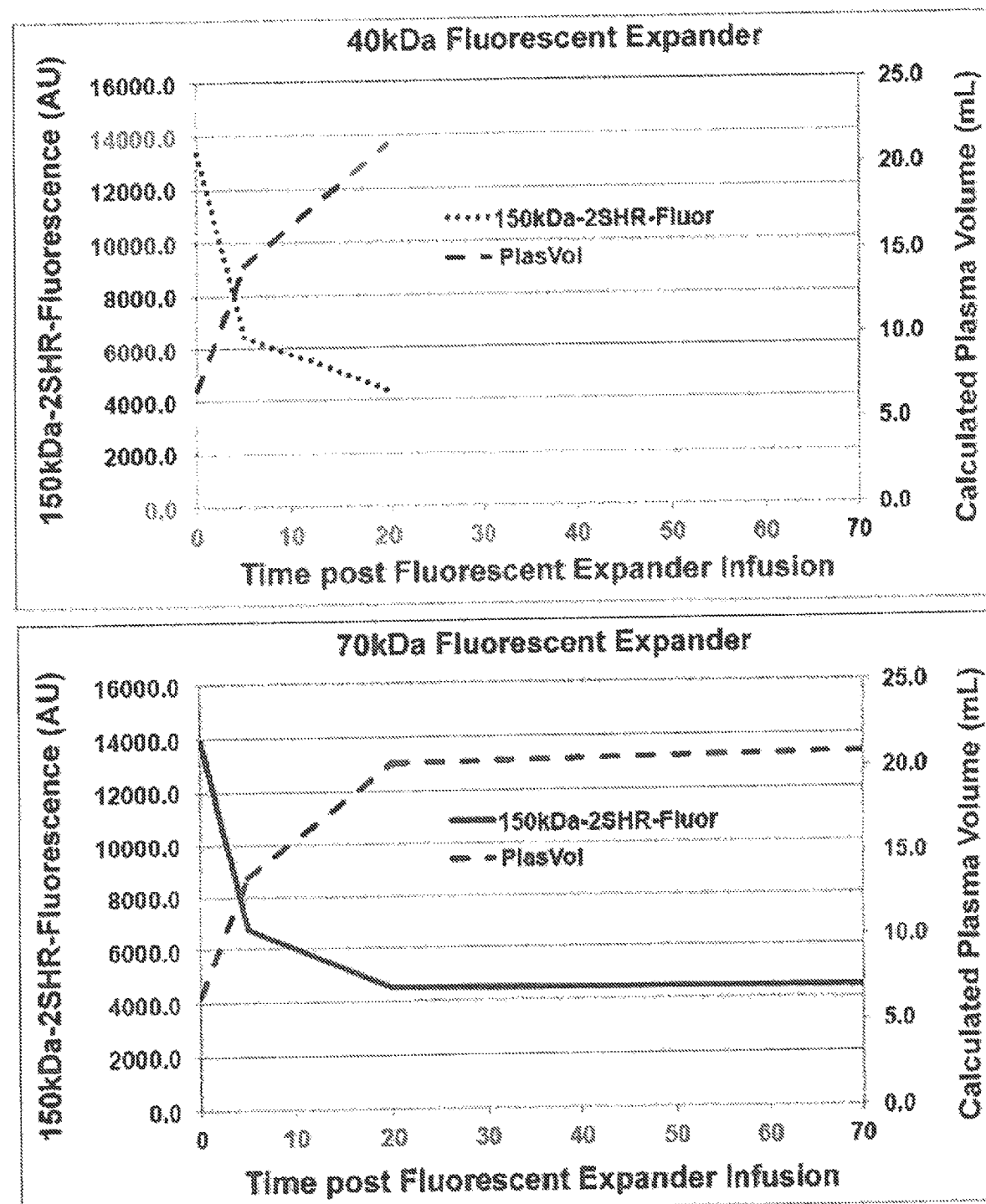
FIG. 4 is a graph showing the relationship between static marker fluorescence and plasma volume in the presence of two exemplary volume expanders: a 40 kDa dextran spiked with a tracer FITC 40 kDa dextran, and a 70 kDa dextran spiked with a tracer FITC 70 kDa dextran.

FIG. 4 shows that when using the static 2SHR 150 kDa marker to measure plasma volume, an increase in plasma volume caused by the volume expanders results in a decrease in the fluorescence of the static marker as it becomes more diluted.

The compositions, uses thereof and methods described herein allow for the rapid determination of blood plasma levels. This facilitates the adjustment of patient fluid levels, such as the amount of blood plasma expander is required by the patient. This, in turn, can prevent renal damage due to a decrease in tubular flow as a result of renal blockage and stasis (the cessation of urinary excretion) which require adequate hydration as a treatment modality.

While the invention has been illustrated and described in detail in the drawings and foregoing description, this is to be considered as illustrative and not restrictive in character. It is understood that one of ordinary skill in the art could readily make changes and modifications to the above-described embodiments and that it would be impractical to attempt to describe all such embodiment variations in the present specification. Accordingly, it is understood that all such changes and modifications that come within the spirit of the invention are desired to be protected.

What is claimed is:

1. A blood volume expander composition comprising
an unmodified protein, unmodified colloid or unmodified crystalloid, and
an indocyanine green (ICG)-labeled protein, colloid comprising ICG or crystalloid comprising ICG having a first excitation wavelength and a first emission wavelength, said indocyanine green (ICG)-labeled protein, colloid comprising ICG or crystalloid comprising ICG being dynamic within the patient, wherein the indocyanine green (ICG)-labeled protein, colloid comprising ICG or crystalloid comprising ICG is present in an amount of from about 0.01% to about 10.0% by weight of the unmodified protein, unmodified colloid or unmodified crystalloid.

2. The blood volume expander of claim 1, wherein said protein of said unmodified protein and said indocyanine green (ICG)-labeled protein is albumin.

3. The blood volume expander of claim 1, wherein said crystalloid of said unmodified crystalloid and said crystalloid comprising ICG is normal saline or lactated Ringer's solution.

4. The blood volume expander of claim 1, wherein said colloid of said unmodified colloid and said colloid comprising ICG is selected from the group consisting of gelatin, hetastarch and dextran.

5. The blood volume expander of claim 4, wherein said colloid of said unmodified colloid and said colloid comprising ICG is dextran.

6. The blood volume expander of claim 5, wherein the dextran comprising ICG is a dynamic molecule with a molecular weight of less than about 75 kDa.

7. The blood volume expander of claim 5, wherein the umodified dextran is Dextran 40, Dextran 70 or Dextran 75.

8. The blood volume expander of claim 5, wherein the dextran comprising ICG is prepared by conjugating dextran with ICG.

9. A method for measuring and maintaining blood volume in a patient comprising the steps of
administering a fluorescently-labeled static molecule to the vascular system of a patient, said static molecule having a second excitation wavelength and a second emission wavelength, said static molecule being non-metabolized within the patient,
obtaining a first blood sample from the patient or making a first non-invasive measurement of the blood of the patient after the static molecule has reached a fully distributed steady state concentration in the vascular system, and calculating the initial plasma volume based on the emission level in the sample,
administering a blood volume expander to the vascular system of the patient, wherein the blood volume expander comprises an unmodified protein, unmodified colloid or unmodified crystalloid and an ICG-labeled protein, colloid comprising ICG or crystalloid comprising ICG having a first excitation wavelength and a first emission wavelength and having a molecular weight similar to, approximately identical to or identical to the molecular weight of the unmodified protein, unmodified colloid or unmodified crystalloid, wherein the ICG-labeled protein, colloid comprising ICG or crystalloid comprising ICG is present in an amount of from about 0.01% to about 10.0% by weight of the unmodified protein, unmodified colloid or unmodified crystalloid,
obtaining additional blood samples or non-invasive measurements from the patient following administration of the blood volume expander,
measuring the loss of blood volume expander from the patient.

10. The method of claim 9, further comprising adding supplemental blood volume expander to the patient as needed.

11. The method of claim 9, wherein the blood volume expander is the blood volume expander of claim 1.

12. The method of claim 9, wherein a series of additional blood samples are taken from the patient or a series of additional non-invasive measurements are made at time intervals of between about 10 and 20 minutes.

13. The method of claim 12, wherein the additional blood samples are continuously taken through an indwelling venous catheter or the additional non-invasive measurements are continuously made using an optical sensor.

14. The method of claim 9, wherein the patient is suffering from kidney disease, acute renal failure or chronic renal failure.

15. The method of claim 9, wherein the fluorescently-labeled static molecule is a dextran with a molecular weight greater than about 75 kDa.

16. The method of claim 9, wherein the fluorescently-labeled static molecule is a dextran with a molecular weight of 150 kDa.

17. The method of claim 9, wherein the fluorescently-labeled static molecule is labeled with 2-SulfhydroRhodamine (2SHR).

18. The blood volume expander of claim 6, wherein the dextran comprising ICG has a molecular weight of about 40 kDa.

* * * * *